(12) United States Patent
Sunkara et al.

(10) Patent No.: US 8,951,506 B2
(45) Date of Patent: Feb. 10, 2015

(54) FORMULATION AND METHOD FOR TREATMENT OF TEETH

(76) Inventors: Sasi Kumar Sunkara, Buffalo, NY (US); Sebastian G. Ciancio, Eggertsville, NY (US)

(*) Notice: Subject to any disclaimer, the term of this patent is extended or adjusted under 35 U.S.C. 154(b) by 534 days.

(21) Appl. No.: 12/743,854

(22) PCT Filed: Nov. 20, 2008

(86) PCT No.: PCT/US2008/012972
§ 371 (c)(1),
(2), (4) Date: Nov. 1, 2010

(87) PCT Pub. No.: WO2009/067237
PCT Pub. Date: May 28, 2009

(65) Prior Publication Data
US 2011/0044892 A1    Feb. 24, 2011

Related U.S. Application Data

(60) Provisional application No. 60/989,393, filed on Nov. 20, 2007.

(51) Int. Cl.
| | | |
|---|---|---|
| A61K 8/00 | (2006.01) | |
| A61K 8/19 | (2006.01) | |
| A61Q 11/00 | (2006.01) | |
| A61C 5/04 | (2006.01) | |

(52) U.S. Cl.
CPC . *A61K 8/19* (2013.01); *A61Q 11/00* (2013.01); A61C 5/04 (2013.01)
USPC ........................................................ 424/49

(58) Field of Classification Search
None
See application file for complete search history.

(56) References Cited

U.S. PATENT DOCUMENTS

| | | | |
|---|---|---|---|
| 4,199,563 A * | 4/1980 | Muhlemann | 424/49 |
| 4,218,434 A * | 8/1980 | Rolla et al. | 424/49 |
| 5,244,651 A | 9/1993 | Kayane et al. | |
| 5,520,725 A | 5/1996 | Kato et al. | |
| 5,653,964 A | 8/1997 | Herms et al. | |
| 5,718,885 A | 2/1998 | Gingold et al. | |
| 5,858,333 A | 1/1999 | Winston et al. | |
| 6,034,152 A | 3/2000 | Burger et al. | |
| 7,090,722 B2 | 8/2006 | Budd et al. | |
| 7,156,911 B2 | 1/2007 | Kangas et al. | |
| 2003/0109491 A1 | 6/2003 | Ulmer et al. | |
| 2004/0126331 A1 * | 7/2004 | Corcoran et al. | 424/49 |
| 2007/0077538 A1 | 4/2007 | Musikant et al. | |
| 2007/0196288 A1 | 8/2007 | Sunkara et al. | |
| 2008/0287566 A1 | 11/2008 | Musikant et al. | |
| 2009/0208909 A1 * | 8/2009 | Rusin et al. | 433/217.1 |

FOREIGN PATENT DOCUMENTS

| | | |
|---|---|---|
| WO | WO2007038764 | 5/2007 |
| WO | WO2007100541 | 8/2007 |

OTHER PUBLICATIONS

S. Ciancio, "Chemical Agents: Plaque Control, Calculus Reduction and Treatment of Dentinal Hypersensitivity," Periodontology 2000, 1995, pp. 75-86, vol. 8.
K. Agee et al, "Effects of Acids and Additives on the Susceptibility of Human Dentine to Denaturation," J. Oral Rehabilitation, 2000, pp. 136-141, vol. 27, Blackwell Science, Ltd.
J. Greenhill et al, "The Effects of Desensitizing Agents on the Hydraulic Conductance of Human Dentin in vitro," J. Dent Res, 1981, pp. 686-698, vol. 60 (3).
D. Pashley et al, "The Effects of Oxalate Treatment on the Smear Layer of Ground Surfaces of Human Dentine," Arch Oral Biol, 1985, pp. 731-737, vol. 30 (10), Pergamon Press Ltd.
J. Pereira et al, "Effect of Desensitizing Agents on the Hydraulic Conductance of Human Dentin Subjected to Different Surface Pretreatments—an in vitro study," Dental Materials, 2005, pp. 129-138, vol. 21, Elsevier Ltd.
W. Vanuspong et al, "Cervical Tooth Wear and Sensitivity: Erosion, Softening and Rehardening of Dentine; Effects of pH, Time and Ultrasonication," J. Clin. Periodontology, vol. 29(4), pp. 351-357.
T. Moeller et al, "The Basicity Characteristics of Scandium, Yttrium, and the Rare Earth Elements," Chemical Reviews, 1945, vol. 37(1), pp. 97 to 159.
J. Hindrichs, "The Role of Dental Calculus and Other Predisposing Factors," Carranza's Clinical Periodontology by Newman et al, 10th ed, 2006, pp. 170-192.

* cited by examiner

*Primary Examiner* — Snigdha Maewall
(74) *Attorney, Agent, or Firm* — James C. Simmons

(57) ABSTRACT

Tooth dentin is treated by applying thereto a paste or other solution to effect plugging of the tubules to eliminate or reduce tooth sensitivity. The solution may be applied to other tooth components for treatment thereof. The solution has a lanthanide salt dissolved therein and a pH between about 6 and 7 and includes an agent for bulking so as to enhance the plugging effect. A dental restoration has incorporated therein lanthanide ions.

10 Claims, 1 Drawing Sheet

FORMULATION AND METHOD FOR TREATMENT OF TEETH

This application is a continuation-in-part of U.S. patent application Ser. No. 11/708,731, filed Feb. 21, 2007, which claims priority of U.S. provisional application 60/776,117, filed Feb. 23, 2006, and U.S. provisional application 60/817,546, filed Jun. 29, 2006, and this application further claims priority of U.S. provisional application 60/989,393, filed Nov. 20, 2007, and all of the above applications are hereby incorporated herein by reference. Contrary to what is stated in the aforesaid U.S. patent application 11/708,731 as filed (published application 2007/0196288), FIG. 6 thereof is an SEM of the dentinal tubule of the dentinal slice shown in FIG. 11; FIG. 7 thereof is a back scattered image of the dentinal tubule shown in FIG. 6, with the gadolinium compound appearing as bright areas; FIG. 12 thereof is an SEM of the dentinal tubule of the dentinal slice shown in FIG. 5; and FIG. 13 thereof is a back scattered image of the SEM shown in FIG. 12.

The present invention is generally related to the treatment of teeth. More particularly, the present invention relates to the maintenance of the integrity of or protection of the dentin against its exposures to the environment and including the prevention or reduction of tooth hypersensitivity and further including the process of mineralization.

Referring to FIGS. 1 and 2, a human tooth 10, shown schematically for purposes of ease of illustration, comprises a hard bone-like material called dentin 12 which encases the pulp chamber 14 and root canal 16. The pulp chamber 14 and root canal 16 contain the dental pulp, illustrated at 18, which comprises blood vessels, connective tissue, and nerve axons. A protective enamel crown 20 covers the outer surface of the dentin 12. A thin protective relatively soft bony tissue called cementum 22 covers the inner surface of the dentin 12. The cementum 22 meets the enamel 20 in a line which surrounds the tooth 10 and which is known as the cemento-enamel junction, illustrated at 24. The cementum 22 is encased in a bone structure 26, and the periodontal ligament 28 is received between the cementum 22 and the bone structure 26. The gingiva portion 30 of the gum normally covers the inner or cervical edge portion of the enamel 20 thereby protecting the cemento-enamel junction 24.

The dentin 12 is composed of tiny or microscopic hollow tubules 32 (only a few illustrated in FIGS. 1 to 3 for ease of illustration) which lie side-by-side running parallel to each other in a direction from the pulp chamber 14 and root canal 16 to the dentin exterior surface, illustrated at 34. The tubules 32 allow the absorption by the dentin 12 of impacts. The tubules 32 are open at one end to the pulp 18. Nerve coverings or odontoblasts (not illustrated), which connect with nerve axons in the pulp 18, project into the tubules 32. The hollow tubules 32 are also open at the other end at the dentin exterior surface 34.

Tooth sensitivity, characterized by short sharp pain arising from exposed dentin in response to stimuli—typically thermal, evaporative, tactile, osmotic, or chemical, is a common complaint. While the exact mechanism of stimulus transmission across dentin is currently unknown, in accordance with what is known as the hydrodynamic theory of tooth sensitivity, exposed dentin is sensitive to such stimuli because these stimuli cause movement of fluid in the odontoblast projections, and this movement is sensed by nerve endings in the pulp 18 which connect with the odontoblasts. Normally, the outer dentin surfaces 34 are protected from exposure to the environment and the resultant entry of fluids into the hollow tubules 32 by their being securely covered by the enamel 20, the cementum 22, and the gum 30. However, if any of these are breached exposing the portion of dentin 12 to the environment, fluids may enter the tubules causing sensitivity or hypersensitivity in accordance with the hydrodynamic theory. Such a breach in the enamel 20, due to trauma or otherwise, is illustrated at 36 in FIG. 1. The cementum 22 may also be breached to allow environmental exposure to tubules 32 by, for example, recession of the gum 30 and improper brushing thereby eroding the soft cementum 22. A cavity, illustrated at 38 in FIG. 3, also constitutes a breach. It is accordingly considered desirable to correct such breaches by closing off exposure of the tubules 32 to the environment.

Dentinal hypersensitivity has been treated by a number of agents which are claimed to reduce pain either by occluding the dentine tubules or by altering the sensory nerve activity at or near the pulpo-dentinal surface. See Ciancio, S. G. (one of the inventors of the present invention), "Chemical Agents: Plaque Control, Calculus Reduction and Treatment of Dentinal Hypersensitivity," *Periodintology 2000*, vol. 8, pp 75-85, 1995, and Pashley, D. H. and Galloway, S. E., "The Effects of Oxalate Treatment on the Smear Layer of Ground Surfaces of Human Dentine," *Arch Oral Biol*, vol. 30, pp 731-737, 1985. One way of treating this condition is by restoring the integrity of the dentin so that the tubules are not exposed to the environment. Greater emphasis has been placed on soothing the nerves than with blocking or plugging of the tubules or the pH of the substance used.

With regard to tubule plugging or closing off of the openings, potassium oxalate and potassium nitrate have been tried but do not give results which are considered to be as effective as desired. See Pereira et al, "'Effect of Desensitizing Agents on the Hydraulic Conductance of Human Dentin Subjected to Different Surface Pre-treatments—an in Vitro Study," *Dent Mater*, vol. 21, pp 129-138, 2005, and Greenhill, J. D. and Pashley, D. H., "The Effects of Desensitizing Agents on the Hydraulic Conductance of Human Dentin in Vitro," *J Dent Res*, vol. 60, pp 686-698, 1981. The high acidity of potassium oxalate (as well as other solutions or substances with high acidic pH such as a pH of 2) may undesirably affect the pulp (vital tissue) as well as undesirably alter the structures of the dentin by initial dissolution (demineralization) due to acidic pH.

The use of glutaraldehyde for reducing dental sensitivity is considered undesirable since it is a poison and undesirably fixes tissues.

U.S. Pat. No. 4,199,563 discloses an inorganic and/or organic cerium salt in aqueous and/or organic solution for sealing and covering dental (including exposed dentin) injuries. It is stated that "aqueous solutions of cerous acetate with pH-values of 5.0 to 8.0 are preferred." The lower part of this pH range is so acidic that it may undesirably demineralize tooth surface.

Also disclosed in this U.S. Pat. No. 4,199,563 is a hard tooth substance treatment pack which includes the cerium salt which is first applied. A mineralizing solution is then applied, which can include calcifying solutions with pH values of from 6.0 to 8.0, fluoride solutions, solutions containing fluoride ions and phosphate ions, and sodium monofluorophosphate. The use of this pack undesirably requires that the cerium and mineralizing solutions be applied successively (see col. 2, lines 20 to 24, of this patent).

Also disclosed in this U.S. Pat. No. 4,199,563 is a pharmaceutical composition comprising the cerium salt in the presence of one or more of a preservative or antiseptic agent, a flavouring agent, a surface active agent, a sweetener, a thickener, an abrasive agent, a colouring agent, and a filler.

U.S. Pat. No. 4,218,434 discloses a composition for cleaning teeth by applying thereto a cation of a lanthanide in the form of a toothpaste having an aqueous base, an abrasive, a binder, a thickener, a surfactant, a humectant, a flavouring agent, and a sweetening agent, or in other forms including mouthwash, tooth powder, chewing gum, or oral spray.

Other references which may be of interest to the present invention include U.S. published applications 2003/0109491 and 2007/0077538.

All of the above U.S. patents and published patent applications are hereby incorporated herein by reference.

It is accordingly an object of the present invention to provide an effective formulation and method for eliminating or reducing dentinal sensitivity.

It is another object of the present invention to provide such a formulation and method which retains tooth integrity, including re-mineralization.

It is a further object of the present invention to provide such a formulation and method wherein the formulation may be applied easily and conveniently, i.e., without the necessity of application of two parts in two successive stages.

It is yet another object of the present invention to include the use of the formulation in, for example, pulp capping, cavity liners, dental restorations, dental adhesive materials, and oral moisturizers and rinses.

The above and other objects, features, and advantages of the present invention will be apparent in the following detailed description of the preferred embodiment thereof when read in conjunction with the appended drawings in which the same reference numerals depict the same or similar parts throughout the several views.

DETAILED DESCRIPTION OF THE PREFERRED EMBODIMENT(S)

The use of "we" or "our" herein is meant to refer to one or both of us.

Figure 1:
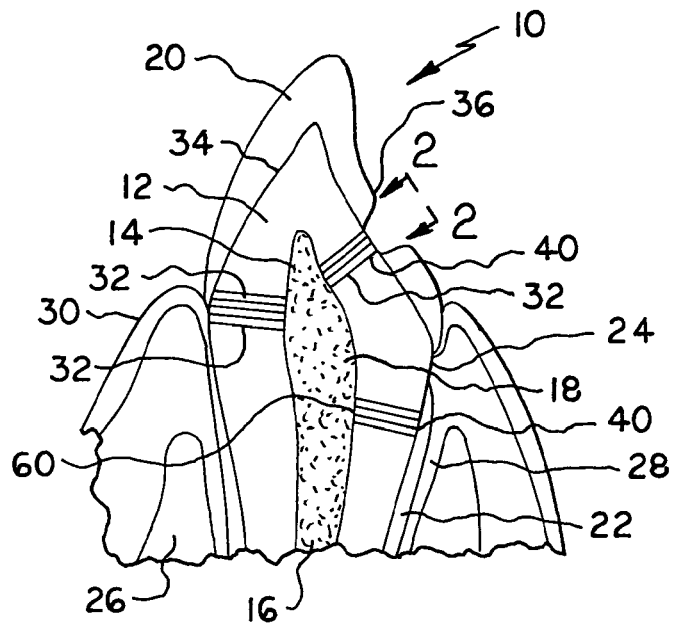
FIG. 1 is a schematic view of a human tooth illustrating a breach in the enamel allowing exposure of the dentin to the environment.
Figure 2:
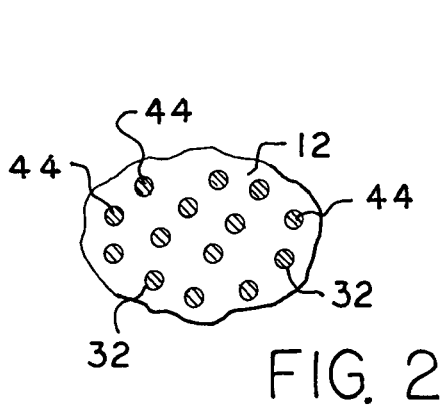
FIG. 2 is a detail schematic view thereof taken along lines 2-2 of FIG. 1 and illustrating schematically the application of a substance in accordance with the present invention to plug or block the dentin tubules.
Figure 4:
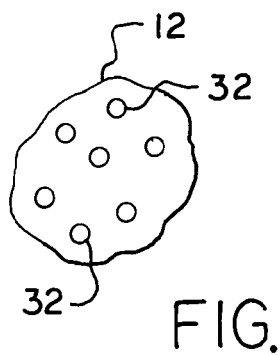
FIG. 4 is a view similar to that of FIG. 2 illustrating the tubules not plugged with the substance.
Figure 3:
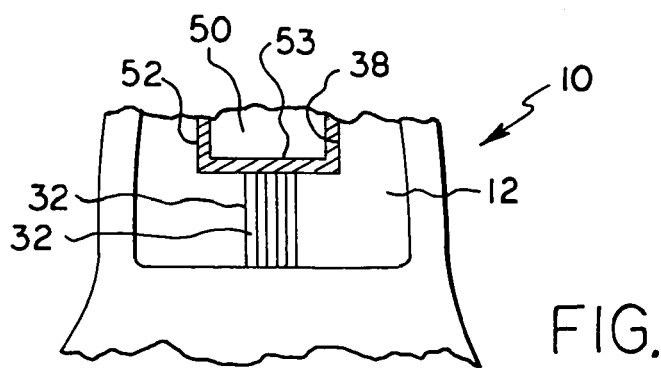
FIG. 3 is a schematic view of a human tooth illustrating the application of a filling in a cavity and the application of a substance in accordance with the present invention to block the dentin tubules.

Referring to FIGS. 1 to 3, a portion of the surface 34 of dentin 12 which is exposed to the environment such as by breach 36 is treated to effect a binding to the tubules 32 to close or plug their exposed ends, illustrated at 40, by applying to the breached dentinal surface a formulation comprising at least one lanthanide salt received in solution in a solvent (i.e., a solvent such as water or other liquid in which the lanthanide salt is soluble). Without wishing to be bound by theory here or elsewhere in this specification, it is our belief, based on hereinafter described blocking of the tubules and the respective chemical structures, that the binding and resulting plugging of the tubule ends results from the chemical binding of the lanthanide cations to the phosphate anions and perhaps also to carbonate ions and proteins in the surrounding environment. The tubular openings are thusly blocked, as we further theorize, to restore integrity to the exposed dentin surface to prevent entrance to the tubules 32 of fluids from the environment and thereby alleviate or reduce the tooth sensitivity. The lanthanide phosphates thus formed are illustrated schematically at 44 in FIG. 2 and are illustrated to be formed to desirably close the tubule openings, FIG. 4 illustrating the tubules 32 unblocked and thus open.

We assessed the role on dentinal tube plugging (i.e., plugging the ends of the tubules for the purpose of sealingly closing them against the entrance of fluids from the environment) of lanthanide group salts (received from Sigma-Aldrich Corporation) in solution (the solvent being water except where otherwise stated), including cerium chloride heptahydrate (99.9% pure), lutetium chloride hexahydrate (99.9% pure), samarium chloride hexahydrate (99% pure), gadolinium chloride hexahydrate (99% pure), gadolinium nitrate hexahydrate (99.9% pure), and lanthanum chloride heptahydrate (99.9% pure). We also assessed other lanthanide compounds, as hereinafter discussed. We used Super Seal that contains potassium oxalate as active ingredient and the desensitizer, potassium nitrate, as controls.

For each of the lanthanide salts, caries-free surgically-extracted human molar teeth were cleaned of organic material and, after removal of the crown, sectioned mesio-distally to provide one to two 1-mm dentine discs which were used in the experiment immediately. These discs were etched with 35% phosphoric acid (Ultra-Etch; Ultradent Products, Inc.) for 10 to 15 seconds and rinsed under tap water (Agee et al, "Effects of Acids and Additives on the Susceptibility of Human Dentine to Denaturation," *Journal of Oral Rehabilitation*, vol. 27, pp 136-141, 2000). A solution containing a respective one of the above-mentioned lanthanide salts in a concentration of 4% to 5% by weight in the solvent was placed on or in contact with the discs respectively for 5 to 10 minutes before rinsing under flowing tap water. These treated discs were dried completely and then split using pliers, this helping to expose the tubular area for observation of depth of penetration. Specimens were then carbon-coated before examination under SEM (scanning electron microscope). The same procedure was used for each of the other lanthanide compounds hereinafter discussed.

The treated dentine slices were then examined for material deposited on the surface of the dentin and within the tubules by using scanning electron microscope (0.5 eV electron beam that can penetrate up to a depth of 10 nm that images surface) and backscattered SEM imaging (20 KeV electron beam that can penetrate up to a depth of 0.5 microns that provides contrast information related to the density of the materials imaged) to image the presence of deposited material, and energy dispersive X-ray (EDX) microanalysis (20 KeV electron beam that can penetrate up to a depth of 1 micron to produce X-rays characteristic of the respective element) to confirm the presence of the respective lanthanide or other element. When observed in a backscattered electron beam, dense materials appear as high contrast (bright areas) material relative to the background material (tooth structure). Lanthanides in general have greater density compared to the hydroxyapatite present in the tooth. Thus, in a backscattered electron beam, the lanthanides appear as bright areas due to their high density compared to the background.

Qualitative SEM examination results, after the application of respective lanthanide salts, show deposits of these materials on the surface of and within the tubules, as illustrated schematically at 44 in FIG. 2, as more particularly described hereinafter.

In our aforesaid patent application Ser. No. 11/708,731 (published application 2007/0196288), we showed in FIGS. 5 (SEM image of dentine surface), 12 (SEM image of tubules), and 13 (back scattered SEM image of the tubules) thereof images we obtained of the dentin slices to which the gadolinium nitrate solution was applied. The images show deposits of gadolinium substantially covering the dentinal surface and penetration (up to about 5 microns) within the tubules and giving the appearance of substantially complete blockage or plugging of the tubules, and the presence of gadolinium was confirmed by EDX.

The cerium chloride, samarium chloride, gadolinium chloride, and lanthanum chloride salts dissolved in water were assessed similarly to cover substantially the dentinal surface (except for lanthanum which was assessed to cover some of the surface) and penetrate into the tubules to various depths up to about 5 to 12 microns (micrometers) and were observed to give the appearance of substantially complete blockage or plugging of the tubules (the lanthanum concentrating more in the tubules up to about 12 microns), and the presence of the respective lanthanide was confirmed by EDX.

The similar observations between gadolinium chloride and gadolinium nitrate are indicative that, for a soluble salt, the type of anion has little or no influence on the tubule binding capacity.

We were not able to assess complete blockage of the tubules by lutetium, although lutetium was observed to penetrate and line the walls of the tubules up to a depth of about 12 microns, and the presence of lutetium (consistently, a lesser amount thereof) was confirmed by EDX. However, we believe that lutetium does have the ability of blocking or plugging tubules when combined with other materials with a binder as hereinafter described to form greater bulk, based on the observed ability of lutetium to attach to the tubule walls.

In comparison of the SEM results with the control, potassium oxalate, it was observed, as seen in FIG. 8 of our aforesaid patent application Ser. No. 11/708,731 (published application 2007/0196288), potassium oxalate formed crystals that appear to block the tubules, and a substantial amount of potassium oxalate was deposited on the dentin surface. The potassium oxalate crystals only penetrated a short distance of up to about 3 to 4 microns, thus indicating that the lanthanides would be more effective for blocking or plugging the tubules. These observations with potassium nitrate are consistent with the earlier observations reported in the above-cited Greenhill and Pashley 1981 article. Moreover, potassium oxalate has an undesirably strong acidic property (pH of about 2).

In comparison of the SEM results with the control, potassium nitrate, there were considerable deposits on the surface with potassium nitrate, but we observed little or no deposits within the tubules, thus indicating that it is unlikely that potassium nitrate would be effective for tubule blockage. These observations with potassium nitrate are consistent with the earlier observations reported in the above-cited Greenhill and Pashley 1981 article.

We also similarly tested gadolinium nitrate (200 mM) in alcohol solvent (Pharmaco), and our observations were similar to those of gadolinium nitrate in water.

We also similarly tested gadolinium chloride (200 mM) in sulfosalicylic acid (Sigma-Aldrich) solvent, and our observations were similar to those of gadolinium chloride in water.

We also similarly tested elemental gadolinium (99.9% pure, 40 mesh) in a mixture of water and sulfosalicylic acid (has a very acidic pH similar to that of potassium oxalate). As seen in FIGS. 9 and 10 of our aforesaid patent application 11/708,731 (published application 2007/0196288), we observed substantially complete coverage and penetration of the tubules up to a depth of about 6 microns.

We also similarly tested elemental gadolinium (99.9% pure, 40 mesh) in a mixture of alcohol and sulfosalicylic acid (has a very acidic pH similar to that of potassium oxalate). As seen in FIGS. 11, 6, and 7 of our aforesaid patent application 11/708,731 (published application 2007/0196288), we observed substantially complete coverage and penetration of the tubules up to a depth of about 13 microns, and the plugging did not seem to be as clear.

We also similarly tested lanthanum hydroxide and lanthanum carbonate in water, and no dentin surface deposits were observed, and there was poor penetration of the tubules with no plugging observed. This can be accounted for by these salts not being soluble in water. For the purposes of this specification and the claims, the term "soluble" refers to a characteristic of a salt of dissolving in water (or other solvent in which the salt is placed) to the extent that there is substantially no precipitation or settling out of material.

In conclusion, the test results show that the lanthanide-based soluble salts tested were effective to apply to dentine to restore integrity thereto (i.e., block the tubule exposure to the environment) and thus prevent or reduce sensitivity resulting from the loss of integrity.

The lanthanide series comprises 15 elements (lanthanum, cerium, praseodymium, neodymium, promethium, samarium, europium, gadolinium, terbium, dysprosium, holmium, erbium, thulium, ytterbium, and lutetium) having atomic numbers 57 through 71 respectively. We assessed two elements at the beginning of the series (i.e., lanthanum and cerium having atomic numbers 57 and 58 respectively), two in the middle of the series (i.e., samarium and gadolinium having atomic numbers 62 and 64 respectively) and one at the end of the series (i.e., lutetium having atomic number 71), all of which were assessed to have tubule binding effectiveness. All of the lanthanide elements have properties which are predictive of their similarly effectively binding to the tubules. The tubules are composed of calcium phosphate. Thus, in order to effectively bind, the lanthanide cation (all the lanthanides being ionic and react readily with most non-metals) must, we believe, bind to a phosphate ion in addition to carbonates and proteins and perhaps other dentin substances. In doing so, it is also our belief that it may displace a calcium cation. Thus, while the binding strength may vary, it is our belief that all of the lanthanide cations bind to phosphate and desirably have a size approximating that of calcium which we believe they may be displacing. Moreover, all of the lanthanides have high melting points (allowing them to be worked with at room or ambient temperatures) and have high coordination numbers (allowing a lanthanide cation to bind desirably and more effectively to a large number of phosphate or other ions at the same time). Thus, while not all the lanthanides were assessed, a sufficient sampling was assessed to provide a high level of confidence that similar results would obtain with the untested lanthanide elements, especially since all of the lanthanides have the same critical properties needed for effective binding to the tubules.

For binding effectiveness, the lanthanide cations must be in solution for binding to the phosphate anions. As discussed above, the lanthanides are placed in solution as salts. Since it is the lanthanide cations that bind and since any lanthanide salt will when dissolved release lanthanide cations, it does not matter what the salt anions are since they do not have a significant role with regard to binding. Moreover, some tests were conducted in which the effects of different soluble salts of the same lanthanide, i.e., nitrate and chloride of gadolinium, were assessed, and, as stated above, this did not significantly change the deposition on the surface of as well as within the tubules. Thus, while not all the salts were assessed, a sufficient sampling was assessed to provide a high level of confidence that similar results would obtain with the untested salts especially in view of the binding strength being dependent on the lanthanide cations and not on the anions.

For binding effectiveness, the lanthanide cations must be in solution so as to achieve binding, and it thus does not matter what the solvent is as long as the solvent has the ability to dissolve the lanthanide salt, producing the needed lanthanide cations for achieving the desired bonding. As discussed hereinafter, while a soluble salt is required, the final formulation can be a gel or paste or gum or the like. Moreover, as discussed above, gadolinium nitrate was assessed in alcohol as well as water, and gadolinium chloride was assessed in sulfosalicylic acid as well as water to check for any role of a different type of solvent. While we believe that the solution in which these compounds were mixed had influence on the physical structure of deposits and depth of penetration, nevertheless the observations were similar showing that binding effectiveness was achieved no matter what the solvent. Thus, while not all solvents were assessed, a sufficient sampling was assessed to provide a high level of confidence that similar results would obtain with untested solvents especially in view of the binding strength being dependent on the lanthanide cations being in solution, no matter what the solvent.

A solution of gadolinium nitrate in water may have an acidic pH of about 4.3. If the solution applied to the dentin is too acidic, for example, lower than 5.5, it will demineralize and thereby undesirably weaken the dentin. If the solution applied to the dentin is too basic, for example, in excess of 7.5, it will undesirably form a lot of calculus. An ideal pH for the dentin treatment solution is considered to be about 6 to 7, preferably about 6.6 to 7. Such a pH is believed to be important not only to prevent de-mineralization but also to aid in re-mineralization of dentin surfaces. Therefore, in accordance with the present invention, the dentin treatment solution is formulated to have a pH of about 6 to 7, preferably about 6.6 to 7.

In order to achieve a dentin treatment solution having a pH of about 6 to 7, an insoluble oxide is applied to the dentin or other tooth surface in addition to the application of the soluble lanthanide salt solution. We have observed experimentally that nano-oxides of gadolinium and cerium, when added to a soluble lanthanide salt solution (gadolinium nitrate, gadolinium chloride, lanthanum nitrate, or lanthanum chloride) and applied to dentin, maintain a constant pH of about 6.6 to 7.0 (important for the desired effect of re-mineralization of the dentin) and also improve the desensitizing capabilities of the solution. The formulation with the addition of the insoluble oxide forms on the surface of the dentin or other tooth surface a protective coat that keeps the pH constant to maintain the tooth integrity and protect its surface from, for example, routinely used acidic beverages, protection of dental restorations, and microleakage protection (protection from bacterial leakage and leakage associated with restorative materials) as well as for re-mineralization. The insoluble oxide may include other insoluble substances providing a pH of about 6 to 7 in the dentin treatment solution and on the dentin surfaces, for example, amphoteric oxides such as aluminum oxide and zinc oxide. The type of soluble lanthanide salt used does not appear to affect the effectiveness of the insoluble oxide added to achieve the desired pH. Thus, a change in anion from nitrate to chloride was not observed experimentally to make any difference.

While the lanthanide salt solution and the insoluble oxide may be applied in separate successive treatments, such an application is considered to be not easy, awkward, and inconvenient. In order to provide a more easily applied formulation, in accordance with the present invention, the lanthanide salt solution and the insoluble oxide are combined with a binder (as well as other ingredients as may be desired, as discussed hereinafter) into a single solution, which may be a paste, gum, or gel or thicker liquid form or other suitable form still containing lanthanide cations, for application to teeth surfaces. For the purposes of this specification and the claims, a "solution" is defined to have any of these other forms.

A suitable treatment formulation for application to dentin, enamel, and cementum for treatment thereof and having a pH between about 6 and 7 may contain the following ingredients. The formulation contains a soluble salt of a lanthanide, for example, a soluble gadolinium salt (ranging from about 1 to 10% by weight, for example, about 5% by weight) in water or other suitable solvent along with a nano oxide (or oxide) of gadolinium or other lanthanide (ranging from about 1 to 10% by weight, for example, about 5% by weight). A thickening agent or other suitable binder (discussed hereinafter) is added to the dissolved lanthanide salt and the insoluble lanthanide oxide such as to prevent the salts from separating out so that they combine into a single application formulation (as opposed to the otherwise having to undesirably apply them in two successive application). The particular composition and form may vary depending on the specific application and may contain other ingredients including, but not limited to, one or more of the various other ingredients discussed hereinafter. Thus, the formulation is a solution which may have any suitable form, such as an aqueous solution or suspension, toothpaste, rinse, gel, gum, mouthwash, prophylaxis paste, toothpowder, pastille, or oral spray (all of which are defined for the purposes of this specification and the claims to be a "solution"). The formulation may, for example, be incorporated into a beverage or nutritional substance such as food or confection or into a public or private water supply. We have experimentally assessed that the solution is compatible with essential oil containing products such as Listerine mouthwash, quaternary ammonium compounds such as cetylpyridinium chloride present in Crest Pro-health toothpaste and chlorhexidine as used for mouth rinses and gels.

For the binder, the formulation may contain, for example, thickening agents such as hydroxypropyl methylcellulose, xanthan gum, methyl cellulose, sodium carboxymethylcellulose, hydroxyethyl cellulose, carrageen, gum karaya, gum tragacanth, gum arabic, and sodium alginate. For example, the formulation may contain about 5% by weight of thickener.

In order to increase bulk to aid in plugging the tubules, fillers such as silicas are preferably incorporated into the formulation. Silicas (silicon dioxide) may, if desired, be incorporated in the formulation as abrasive materials, including, for example, Aerosol 200, Sident 8, Aerodisp 7520, and Sipernat 350 silicon dioxide (all may be obtained from Degussa). The abrasive property may also be achieved by incorporating nanoparticle size of oxides used, for example, gadolinium oxide.

The formulation may contain, for example, flavoring agents such as peppermint, spearmint, and cinnamon and used along with, for example, menthol, wintergreen, clove, lemon, orange, methylsalicylate, licorice, eucalyptus, or other suitable agents. The flavoring agent may vary in an amount, for example, up to 1% to 2% by weight.

The formulation may contain, for example, sweeteners such as, for example, sorbitol (for example, 20% sorbitol and humectant), xylitol, manitol, sodium saccharin, and aspartame.

The formulation may contain, for example, polyol humectants such as sorbitol, substances from polyols such as xylitol and manitol, and other humectants such as propylene glycol and glycerine. For example, the formulation may contain about 10% by weight of humectant.

The formulation may contain, for example, surfactants such as ionic surfactants including sodium dodecyl sulphate, sodium lauryl sulphate, zwitterionic (amphoteric) surfactants including cocamidopropyl betaine, and cationic (based on quaternary ammonium cations) surfactants including cetyl trimethyl ammonium chloride.

The formulation may contain, for example, preservatives such as sodium benzoate and methyl paraben.

The formulation may contain, for example, coloring agents such as titanium dioxide.

The formulation may contain, for example, suitable fluoridating agents.

In accordance with the present invention, the formulation is provided in combination with a sheet of written or printed instructions for application of the formulation to the dentin and/or enamel and/or cementum for tooth treatment.

The following is an example of a specific formulation which we prepared and tested. The formulation is in the form of a paste (clinical or over-the-counter). With all percentages being by weight, the formulation contains (1) 4% to 5% gadolinium nitrate or gadolinium chloride supplied by Sigma-Aldrich, (2) 0.5% titanium dioxide coloring agent (supplied by Kemira under its AFDC 300/AFDC 200), (3) 30% silicon dioxide (silica) filler supplied by Degussa, (4) 2% cocamidopropyl betaine surfactant (supplied by Lonza as its LonzaineCO/SLS/modifications of SLS), (5) 1% spearmint/peppermint/cinnamon flavoring agent supplied by Bell Flavors & Fragrances Inc., (6) 0.1% sodium benzoate preservative (supplied by DSM as its Purox S preservative), (7) 20% Sorbitol/Mannitol/Xylitol sweetener and humectant, supplied by Sigma, (8) 40% water, and (9) 2% hydroxypropyl methylcellulose binder/thickener supplied by Dow Chemical Company as its Methocel K100M premium).

Several formulations were prepared in each of which all of the ingredients except the binder/thickener were first mixed. In a first combination, gadolinium nitrate was used, and the silica used was 7.5% Aerosil 200, 7.5% Sident 8, and 15% Aerodisp 7520. In a second combination, gadolinium chloride was used, and the silica used was 7.5% Aerosol 200, 7.5% Sident 8, and 15% Aerodisp 7520. In these first and second combinations, the pH was about 5.7. In a third combination, gadolinium nitrate was used, and the silica used was 7.5% Aerosol 200, 7.5% Aerodisp 7520, and 15% Sipernat 350. In a fourth combination, gadolinium chloride was used, and the silica used was 7.5% Aerosol 200, 7.5% Aerodisp 7520, and 15% Sipernat 350. In these third and fourth combinations, the pH was about 6.05. Hereinafter, all of these first to fourth combinations will be collectively referred to as the exemplary formulation since similar results were obtained for all of them.

In addition, formulations were prepared and tested which contained only gadolinium chloride, silica compounds, and the Methocel binder, and similar results were obtained as discussed hereinafter for the above first to fourth formulations.

The mixture (except the binder) was continuously stirred as each component was being added. It was mixed thoroughly until an ingredient was completely incorporated and the mixture approached a uniform consistency before the next ingredient was added. While preparing this mix, two-thirds of the total amount of water was used to mix these ingredients. The remaining one-third was used as hot water (heated to 80 to 90 degrees C.) to mix the Methocel (binder) powder. The Methocel (binder) powder was mixed in the hot water thoroughly in order that all the particles were wetted and a consistent dispersion obtained. The Methocel/water component was then added to the rest of the preparation and mixing continued for at least 20 minutes to obtain a uniform paste.

For test/assessment of each of the exemplary formulations, in a first step, caries-free surgically-extracted human molar teeth were cleaned of organic material and, after removal of the crown, sectioned mesio-distally to provide one to two 1-mm dentine discs which were used in the experiment immediately. These discs were etched with 37% phosphoric acid for 10 to 15 seconds and rinsed under tap water (Agee et al, "Effects of Acids and Additives on the Susceptibility of Human Dentine to Denaturation," *Journal of Oral Rehabilitation*, vol. 27, pp 136-141, 2000). The exemplary formulation (paste) was placed for 5 to 10 minutes before rinsing under flowing tap water. During application of the exemplary formulation (paste), discs were also placed in an environment of saliva. In a second step, the cleaned discs were immersed in saliva and left in place for 60 minutes. Later the discs were gently brushed and the first step repeated for three cycles. Then the discs were dried completely and split using pliers, this helping to expose the tubular area for observation of depth of penetration. Specimens were then carbon-coated for examination under SEM.

SEM images thereof showed deposits on the surfaces of the dentin discs and that the exemplary formulation material had entered into the tubules up to about 12 microns and was observed to be very compact therein (an appearance of greater compactness than observed in our previous hereinfore described tests), thus indicating effectiveness of the material for blocking the tubules. We used as a control the same formulation but which lacked gadolinium salt, and SEM images of its application to the dentin discs showed little or no entering or attachment to the tubules, thus indicating non-effectiveness of the control and the requirement/need for the presence of gadolinium or other lanthanide.

It should of course be understood that, preferably, an insoluble lanthanide oxide or other substance which provides a pH (in the presence of an acid or base) between about 6 and 7, preferably between about 6.6 and 7, may be added to the formulation containing the soluble lanthanide salt, and other various ingredients may also be added, and such varied forms of the formulation are meant to come within the scope of the present invention.

Referring to FIG. 3, there is illustrated a filling or restoration 50 received in the cavity 38. In accordance with the present invention, the treatment solution or formulation is prepared as a varnish which is applied as a coating, illustrated at 52, to the walls of the dentally prepared cavity 38 prior to insertion and bonding of the filling 50. As discussed hereinafter, the treatment solution or formulation is also prepared (with changes in the amounts of certain ingredients as compared to the amounts of ingredients for the wall varnish 52, as hereinafter discussed) as a cavity liner 53 to cover the cavity floor. The varnish or coating 52 is provided to prevent bacterial leakage from external fluids (environment) as well as from the filling 50 into the tubules 32. The protective coating 52 which binds to the dentin surface may have insoluble as well as soluble (in water, ethanol, or other suitable solvent) lanthanide salts, including, but not limited to, chloride (easily water soluble), nitrate (easily water soluble), carbonate, hydroxide, fluoride, oxide (insoluble), acetate (water soluble), iodide (water soluble), and sulphate (water soluble), as well as combinations thereof, and formulated to have a pH of about 6 to 7 (preferably about 6.6 to 7) as previously discussed. The formulation of coating 52 may be applied, for example, to the enamel 20, restoration 50, dentin 12, or cementum 22. By forming a coating, it can also act as a mineralizing agent.

According to the site and the purpose of application, the coating 52 may, for example, contain antibacterial agents such as essential oils such as eucalyptus oil, quaternary ammonium compounds, and chlorhexidine, and antibiotics such as tetracycline, and may be formed as a miscible liquid suitable to coat the tooth surface. In this regard, we experimentally assessed the compatibility of eucalyptus oil and gadolinium with the eucalyptus oil in the presence of a soluble salt of gadolinium and its nano oxide. An emulsifying agent (cocamidopropyl betaine, considered to be a very mild agent) along with a binder (carboxymethyl cellulose, required to bind the agents) was found to form a stable formulation. Similarly, we experimentally assessed for interaction with chlorhexidine and quaternary ammonium compound (cetyl trimethyl ammonium chloride). Further, we experimentally assessed the compatibility of pectin, a commonly used component of moisturizers. These materials were assessed to have good compatibility without precipitation. The pH of the coating 52 remained stable, near neutral. The viscosity can be adjusted depending upon the form of delivery. These materials were assessed to form miscible liquids. In order to check interaction of the components of the formulation in coating 52 with many commonly used mouth rinses and moisturizers, a direct mixture of soluble solutions of gadolinium and lanthanum were assessed. In support of our above described assessments, we experimentally assessed that the formulation is compatible with essential oil containing products such as Listerine mouthwash, quaternary ammonium compounds such as cetylpyridinium chloride present in Crest Pro-health mouth rinse, and chlorhexidine as used for mouth rinses and gels. This demonstrated that the formulation should not precipitate contents of other oral hygiene aids or affect their efficacy in people using them. These essential oil, chlorhexidine, and quaternary ammonium containing products form miscible liquid that can be used with gadolinium and lanthanum. In addition to the relationship to compatibility, with our previous finding (see our aforesaid U.S. patent application Ser. No. 11/708,731, published application 2007/0196288) that lanthanides affect *p. gingivalis* proteases, we predict that they may improve the antibacterial properties of the added substances (essential oils, etc.) alongside coating the tooth surfaces to re-mineralize them and protecting from hypersensitivity.

The coating 52 may also be combined with flavoring agents such as spearmint, peppermint, and cinnamon to leave a fresh breath after its application. A preferred formulation is, for example, a mixture of gadolinium nitrate and nano gadolinium oxide in combination with water, carboxymethylcellulose, Canada balsam, and Aerodisp 7520 silica. The varnish may be applied as coating 52 by a dentist in his or her office, by patient home application by use of a brush or by a rinse which can leave a coat on the tooth surface or as a gum or through the use of dental floss.

The filling material 50 may have various compositions including GIC (glass ionomer cement), such as discussed in U.S. Pat. No. 5,520,725 which is incorporated herein by reference, or a composite material having resin. In order to form the filling 50, the dentist conventionally combines a glass powder with a conventional glass-dissolving acid, as known in the art, to form a paste of smooth consistency which the dentist then applies into the prepared cavity space 38 and allowed to harden. In accordance with the present invention, since lanthanides bond with glass particles as well as dentin surfaces, a soluble lanthanide salt (including, for example, soluble salts of lutetium, samarium, gadolinium, cerium, and lanthanum) is incorporated into the glass particles by surface treatment by heating the glass particles in the presence of the lanthanide at high temperature. During the process of mixing with an acid to form a paste, the acid added to the glass particles will leach out the contents of the glass particles. Lanthanides which are surface coated/even present within the glass will leach out. When this paste is applied in the cavity 38, they form a strong bond with the teeth along with other components of the glass.

Lanthanides have the ability to bond to resin, specifically the carboxylic acid functional group in the resin. Accordingly, in accordance with the present invention, soluble lanthanide salts are added to resin-containing composite restorations 50 in order to eliminate or reduce polymerization shrinkage and thus inhibit any changes in the restoration properties.

In accordance with the present invention, soluble lanthanide salts are incorporated into dental adhesive materials to increase their binding capacity and reduce any leakages.

Leakage of irritants from the environment or saliva or from the restoration 50 through the tubules can not only cause hypersensitivity but it can also damage the pulp 18. Further in accordance with the present invention, a cavity liner 53 is used to provide a protective cap or covering to the pulp 18 (liner 53 placed directly in contact with the pulp 18 or placed over a small amount of remaining caries and also in direct contact with the pulp when there is a suspected exposure to the pulp) in deep cavities. The varnish 52 covers the walls of the cavity while the cavity liner 53 covers the floor of the cavity and is generally formulated, in accordance with principles of common knowledge to those of ordinary skill in the art to which the present invention pertains, to have a relatively greater amount of lanthanide salt for greater strength to withstand greater forces and to have a relatively greater amount of binder or thickening agent for greater viscosity.

Calcium hydroxide has been conventionally used as a pulp cap to precipitate out certain components (proteins and minerals) of the pulp to thereby begin a mineralization adjacent the damaged dentin. Dental pulp 18 contains blood vessels and nerves. The extracellular fluid is considered to be similar in composition to that of serum. The interaction of lanthanides with serum and media has been assessed in an experiment designed to simulate a similar environment in a test tube, based on our belief that media provides an environment analogous (not exactly the same but believed to be approximate) to an in vivo (pulp) condition. The osmolarity of the culture media is around 300 mM (millimoles), which approaches the osmolarity of the extracellular fluid in humans. Similar to the calcium hydroxide, lanthanide containing formulations were observed to precipitate proteins as well as ions present in the solution. Lanthanide binding to certain components of the media would precipitate out ions like phosphate ions and proteins from the solution. The precipitate forms a barrier which immediately or later forms a mineralized area, thus indicating the ability of lanthanides to be used as a pulp capping agent.

The high solubility of calcium hydroxide may result in contamination of the bonding agent and increased marginal leakage. To function optimally for many years, a cavity liner should have sufficient strength and resistance to solubility. If a liner is initially used to line the floor of the cavity (completely) and subsequently gets dissolved over time, the net result would be an unsupported restoration. This lack of support could make the restoration more prone to fracture during chewing, thus making the use of calcium hydroxide to line the entire dentin surface under a composite or amalgam restoration undesirable. Moreover, calcium hydroxide doesn't bind to dentin. Accordingly, in accordance with the present invention, soluble lanthanide salts are desirably used along with the insoluble lanthanide oxides (instead of calcium hydroxide) for the cavity liner 53. For cavity liners, the formulation contains, in addition to the soluble lanthanide salts, a binder, and an insoluble lanthanide oxide or other ingredient which provides a pH between about 6 and 7, preferably between about 6.6 and 7, as previously discussed.

In accordance with the present invention, the treatment formulation of the present invention, preferably containing an antimicrobial, is used as a root canal sealant to coat the root canal 16/pulp chamber 18 and thereby attached to and block the inner openings, illustrated at 60, of the tubules 32 to prevent leakage into the root canal.

It should be understood that, while the present invention has been described in detail herein, the invention can be embodied otherwise without departing from the principles thereof, and such other embodiments are meant to come within the scope of the present invention as defined by the appended claims.

What is claimed is:

1. A formulation for application to and retention on teeth to plug tubules thereof and/or for re-mineralization thereof, the formulation consisting essentially of a solvent, a lanthanide salt dissolved in said solvent, and a lanthanide oxide and a binder which binds said lanthanide oxide into the formulation, wherein pH of the formulation is between 6 and 7 and is maintained between 6 and 7 when applied to and retained on teeth to plug tubules thereof and/or for re-mineralization thereof, and wherein said lanthanide oxide is selected from the group consisting of gadolinium oxide, cerium oxide, lanthanum oxide, and samarium oxide.

2. A formulation for application to and retention on teeth to plug tubules thereof and/or for re-mineralization thereof, the formulation consisting essentially of a solvent, a salt dissolved in said solvent, a lanthanide oxide, and a binder for binding said lanthanide oxide to said salt dissolved in said solvent, wherein the formulation includes an agent for increasing bulk of the formulation, said salt being at least one of a lanthanum salt, a praseodymium salt, a neodymium salt, a promethium salt, a samarium salt, a europium salt, a gadolinium salt, a terbium salt, a dysprosium salt, a holmium salt, a erbium salt, a thulium salt, a ytterbium salt, and a lutetium salt, wherein pH of the formulation is between 6 and 7 and is maintained between 6 and 7 when applied to and retained on teeth to plug tubules thereof and/or for re-mineralization thereof, and wherein said lanthanide oxide is selected from the group consisting of gadolinium oxide, cerium oxide, lanthanum oxide, and samarium oxide.

3. A formulation according to claim 1 wherein said lanthanide salt comprises a salt of one of cerium, lutetium, samarium, lanthanum, and gadolinium.

4. A formulation according to claim 1 wherein said pH is maintained between 6.6 and 7, and the formulation further in combination therewith at least one sheet of printed instructions for applying the formulation to a tooth for treatment thereof.

5. A formulation according to claim 2 wherein said lanthanide salt comprises a salt of one of cerium, lutetium, samarium, and gadolinium.

6. A formulation according to claim 1 wherein an amount of said lanthanide oxide in the formulation is between about 1 and 10 per cent by weight.

7. A formulation according to claim 1 which includes an agent for increasing bulk of the formulation.

8. A method for treating teeth to plug tubules thereof and/or for re-mineralization thereof comprising applying to and retaining on a tooth a formulation consisting essentially of a solvent, a lanthanide salt dissolved in the solvent, a lanthanide oxide, and a binder which binds the lanthanide oxide into the formulation, wherein pH of the formulation is between 6 and 7 and is maintained between 6 and 7 while the formulation is applied to and retained on the tooth to plug tubules thereof and/or to re-mineralize the tooth, and wherein said lanthanide oxide is selected from the group consisting of gadolinium oxide, cerium oxide, lanthanum oxide, and samarium oxide.

9. A method according to claim 8 comprising applying the formulation to dentin tubules of the tooth for plugging the tubules.

10. A method according to claim 8 further comprising selecting the formulation to be characterized by providing bulk for increasing dentin tubule plugging capability.

* * * * *